US00PP33576P2

(12) United States Plant Patent
Arts

(10) Patent No.: US PP33,576 P2
(45) Date of Patent: Oct. 26, 2021

(54) RASPBERRY PLANT NAMED 'ABB 127'

(50) Latin Name: *Rubus idaeus*
Varietal Denomination: ABB 127

(71) Applicant: ALLBERRY B.V., De Kwakel (NL)

(72) Inventor: Niels Arts, Aalsmeer (NL)

(73) Assignee: Allberry B.V., De Kwakel (NL)

( * ) Notice: Subject to any disclaimer, the term of this patent is extended or adjusted under 35 U.S.C. 154(b) by 0 days.

(21) Appl. No.: 17/073,376

(22) Filed: Oct. 18, 2020

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 6/7499; A01H 5/08
See application file for complete search history.

*Primary Examiner* — Keith O. Robinson
(74) *Attorney, Agent, or Firm* — C. Anne Whealy

(57) ABSTRACT

A new and distinct cultivar of Raspberry plant named 'ABB 127', characterized by its relatively compact, upright and bushy plant habit; suitability as a potted plant; freely basal branching habit; high fruit production; fruits are produced on prior and current seasons' canes; large reddish orange-colored broadly conical fruits; pleasant and sweet fruit taste; and good fruit postharvest longevity.

2 Drawing Sheets

Botanical designation: *Rubus idaeus.*
Cultivar denomination: 'ABB 127'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Allberry B. V. of De Kwakel, The Netherlands on Dec. 23, 2019, application number 2019/3500. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exemption under 35 U.S.C. 102(b)(1) for disclosure and/or sales prior to the filing date but less than one year prior to the effective filing date.

BACKGROUND OF THE INVENTION

The present Invention relates to a new and distinct cultivar of Raspberry plant, botanically known as *Rubus idaeus* and hereinafter referred to by the name 'ABB 127'.

The new Raspberry plant is a product of a planned breeding program conducted by the Inventor in Rossum, Gelderland, The Netherlands. The objective of the breeding program was to develop new Raspberry plants with good fruit quality, productivity, uniformity and postproduction longevity.

The new Raspberry plant originated from a cross-pollination during the summer of 2011 by the Inventor of *Rubus idaeus* 'Advabertwee', disclosed in U.S. Reissue Pat. No. 46,030 and U.S. Plant Pat. No. 23,914, as the female, or seed, parent with *Rubus idaeus* 'Advabemap' disclosed in U.S. Plant Pat. No. 27,812, as the male, or pollen, parent. The new Raspberry plant was discovered and selected by the Inventor as a single plant from within the progeny of the stated cross-pollination in a controlled environment in Rossum, Gelderland, The Netherlands in September, 2012.

Asexual reproduction of the new Raspberry plant by root cuttings in a controlled environment at Rossum, Gelderland, The Netherlands since the spring of 2013 has shown that the unique features of this new Raspberry plant are stable and reproduced true to type in successive generations of asexual reproduction.

SUMMARY OF THE INVENTION

Plants of the new Raspberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ABB 127'. These characteristics in combination distinguish 'ABB 127' as a new and distinct Raspberry plant:

1. Relatively compact, upright and bushy plant habit; suitable as a potted plant.
2. Freely basal branching habit.
3. High fruit production.
4. Fruits are produced on prior and current seasons' canes.
5. Large reddish orange-colored broadly conical fruits.
6. Pleasant and sweet fruit taste.
7. Good fruit postharvest longevity.

Plants of the new Raspberry differ primarily from plants of the female parent, 'Advabertwee' in plant habit as plants of the new Raspberry are more compact than plants of 'Advabertwee'.

Plants of the new Raspberry differ primarily from plants of the male parent, 'Advabemap' in plant habit as plants of the new Raspberry are more compact than plants of 'Advabemap'.

Plants of the new Raspberry can be compared to plants of *Rubus idaeus* 'Advabereen', disclosed in U.S. Reissue Pat. No. 46,041 and U.S. Plant Pat. No. 23,915. In side-by-side comparisons, plants of the new Raspberry differ from plants of 'Advabereen' in the following characteristics:

1. Plants of the new Raspberry are more compact than plants of 'Advabereen'.
2. Plants of the new Raspberry have smaller terminal leaflets than plants of 'Advabereen'.
3. Plants of the new Raspberry flower and fruit about two weeks earlier than plants of 'Advabereen'.
4. Plants of the new Raspberry produce larger fruits than plants of 'Advabereen'.
5. Fruit drupelets of plants of the new Raspberry are smaller but more uniform than fruit drupelets of plants of 'Advabereen'.

BRIEF DESCRIPTION OF THE PHOTOGRAPHS

The accompanying colored photographs illustrate the appearance of the new Raspberry plant showing the colors as true as it is reasonably possible to obtain in colored reproductions of this type. Colors in the photographs may differ slightly from the color values cited in the detailed botanical description which accurately describe the colors of the new Raspberry plant.

The photograph on the first sheet is a side perspective view of typical fruiting plants of 'ABB 127'.

The photograph on the second sheet is a close-up view of a typical fruit of 'ABB 127'.

DETAILED BOTANICAL DESCRIPTION

The aforementioned photographs, following observations and measurements describe plants grown during the spring, summer and autumn in 10-liter containers in a polyethylene-covered greenhouse in Rossum, The Netherlands and under typical cultural practices of Raspberry plant production. During the production of the plants, day temperatures ranged from 18° C. to 20° C. and night temperatures ranged from 11° C. to 14° C. Plants were one year old when the photographs and description were taken. In the following description, color references are made to The Royal Horticultural Society Colour Chart, 2015 Edition, except where general terms of ordinary dictionary significance are used.

Botanical classification: *Rubus idaeus* 'ABB 127'.

Parentage:

*Female, or seed, parent.*—*Rubus idaeus* 'Advabertwee', disclosed in U.S. Reissue Pat. No. 46,030 and U.S. Plant Pat. No. 23,914.

*Male, or pollen, parent.*—*Rubus idaeus* 'Advabemap', disclosed in U.S. Plant Pat. No. 27,812.

Propagation:

*Type*.—By root cuttings.

*Time to initiate roots, summer*.—About 12 to 14 days at temperatures about 15° C. to 17° C.

*Time to produce a rooted young plant, summer*.—About six weeks at temperatures about 15° C. to 17° C.

*Root description*.—Medium to fine in thickness, fibrous, typically brownish white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Upright and bushy plant habit; vigorous growth habit; rapid growth rate.

*Plant height*.—About 1.2 to 1.6 meters.

*Plant diameter*.—About 40 cm.

Cane description:

*Prior season's canes*.—Length: About 80 cm. Internode length: About 6 cm. Color: Close to 164B, no anthocyanin observed. Time of vegetative bud burst: Typically mid March in The Netherlands. Length of vegetative bud: About 1 cm. Time of cane emergence: Typically April in The Netherlands.

*Current season's canes*.—Length: About 1.4 meters. Internode length: About 6 cm. Color: Close to 143C, no anthocyanin observed. Time of vegetative bud burst: Typically early March in The Netherlands. Length of vegetative bud: Less than 1 cm. Time of cane emergence: Typically March in The Netherlands.

*Strength*.—Strong.

*Aspect*.—Mostly erect.

*Texture*.—Smooth, glabrous; thorny.

*Thorns*.—Density: About three per linear cm. Length: About 1 mm. Width: About 1 mm. Shape: Roughly deltoid. Apex: Acuminate, downwardly sloping. Base: Truncate. Margin: Entire. Color, immature and mature: Close to 144D.

Leaf description:

*Arrangement*.—Alternate; compound with typically three to five leaflets.

*Length, leaf*.—About 28 cm to 32 cm.

*Width, leaf*.—About 22 cm to 26 cm.

*Length, terminal leaflet*.—About 8 cm to 12 cm.

*Width, terminal leaflet*.—About 10 cm to 14 cm.

*Length, lateral leaflets*.—About 10 cm to 14 cm.

*Width, lateral leaflets*.—About 6 cm to 10 cm.

*Leaflet shape*.—Ovate.

*Leaflet apex*.—Cuspidate.

*Leaflet base*.—Terminal leaflets, cordate; lateral leaflets, cuneate.

*Leaflet margin*.—Double serrate.

*Leaflet profile*.—Straight.

*Leaflet texture, upper and lower surfaces*.—Smooth, glabrous; slightly rugose.

*Leaflet venation*.—Pinnate.

*Leaflet color*.—Developing leaflets, upper surface: Close to 144A. Developing leaflets, lower surface: Close to 194B. Fully expanded leaflets, upper surface: Close to 143A; venation, close to 144A. Fully expanded leaflets, lower surface: Close to 194B; venation, close to 147D.

*Petioles*.—Length, leaf: About 7 cm to 8 cm. Diameter, leaf: About 3 mm. Length, terminal leaflet: About 3 cm. Diameter, terminal leaflet: About 3 mm. Length, lateral leaflets: About 3 mm. Diameter, lateral leaflets: About 3 mm. Texture, upper and lower surfaces: Sparsely prickled. Color, upper and lower surfaces: Close to 141A to 141B.

Flower description:

*Flower form and flowering habit*.—Single star-shaped flowers arranged in axillary sprays; freely flowering with about two to five flowers per spray and about four to six sprays per lateral branch; flowers face mostly outwardly; flowers not persistent.

*Fragrance*.—None detected.

*Natural flowering season*.—Typically, in The Netherlands, plants flower in late April on prior season's canes and in July on current season's canes.

*Flower buds*.—Length: About 5 mm to 10 mm. Diameter: About 5 mm to 10 mm. Shape: Roughly deltoid with acuminate apex. Color: Close to 141D.

*Flower diameter*.—About 2.5 cm.

*Flower depth* (*height*).—About 7 mm.

*Petals*.—Arrangement: Single whorl of five petals. Length: About 1.5 cm. Width: About 3 mm to 5 mm. Shape: Lanceolate to somewhat ovate. Apex: Obtuse. Base: Attenuate. Margin: Entire. Texture, upper and lower surfaces: Smooth, glabrous. Color: When opening and fully opened, upper surface: Close to NN155D. When opening and fully opened, lower surface: Close to NN155D.

*Sepals*.—Arrangement: Single whorl of five sepals forming a star-shaped calyx; sepals fused at the base. Calyx length: About 2 cm to 2.5 cm. Calyx width: About 2 cm to 2.5 cm. Length, free part: About 2 cm. Width: About 1 cm; at the apex, about 2 mm. Shape: Deltoid. Apex: Acuminate. Margin: Entire. Texture, upper and lower surfaces: Slightly pubescent. Color: When developing, upper and lower surfaces: Close to 145B. Fully opened, upper and lower surfaces: Close to 145B.

*Peduncles*.—Length: About 5 cm to 10 cm. Diameter: About 1.5 mm. Strength: Strong. Aspect: About 30° from vertical. Texture: Prickled. Color: Close to 145A, no anthocyanin observed.

*Pedicels* (*flowers and fruits*).—Length: About 1 cm. Diameter: About 1 mm. Strength: Strong. Aspect: About 30° from peduncle axis. Texture: Prickled. Color: Close to 145B, no anthocyanin observed.

*Reproductive organs*.—Stamens: Quantity per flower: About 50 or more. Filament color: Close to NN155D. Anther length: About 1 mm. Anther color: Close to 164C and 156C. Pollen amount: Moderate. Pollen color: Close to 196C. Pistils: Quantity per flower: About 100 or more. Pistil length: About 5 mm. Stigma shape: Rounded. Stigma color: Close to NN155D. Style length: About 5 mm. Style color: Close to NN155D. Receptacles: Height: About 1 cm. Diameter: About 1 cm. Shape: Conical. Color: Close to NN155D.

*Fruits* (*aggregate of drupelets*).—Quantity: One per flower. Length of fruiting lateral: About 50 cm on prior and About 70 cm on current seasons' canes. Fruiting lateral aspect: About 45° from vertical on prior season's canes, and about 60° from vertical on current season's canes. Number of drupelets per fruit: About 100 or more. Time of fruit ripening: Typically in The Netherlands, on prior season's canes, fruits ripen in mid May, and on current season's canes, fruits ripen in mid August. Length of fruiting period: In The Netherlands, on prior season's canes, fruits are produced for about seven weeks, and on current season's canes, fruits are produced for about 56 to 60 days. Length: About 2.5 cm to 2.8 cm, fruits produced on prior season's canes are slightly larger than fruits produced on current season's canes. Diameter: About 2.3 cm to 2.5 cm. Shape: Broadly conical. Weight: About 7 grains. Firmness: Very firm. Taste: Pleasant, sweet and agreeable. Luster: Glossy. Adherence to plug: Moderate on prior and current seasons' canes. Postharvest longevity: Good postharvest longevity, fruits last about ten days. Color: Close to 44B. Seeds: Quantity: One per drupelet. Length: About 2.5 mm. Diameter: About 1 mm. Texture: Smooth, glabrous. Color: Close to 20D.

Pathogen & pest resistance: Plants of the new Raspberry have been noted to have low susceptibility to Downy Mildew (*Peronospora sparsa*) and Red Spider Mites (*Tetranychus urticae*).

Temperature tolerance: Plants of the new Raspberry have been observed to tolerate temperatures ranging from 4° C. to 35° C.

It is claimed:

1. A new and distinct Raspberry plant named 'ABB 127' as illustrated and described.

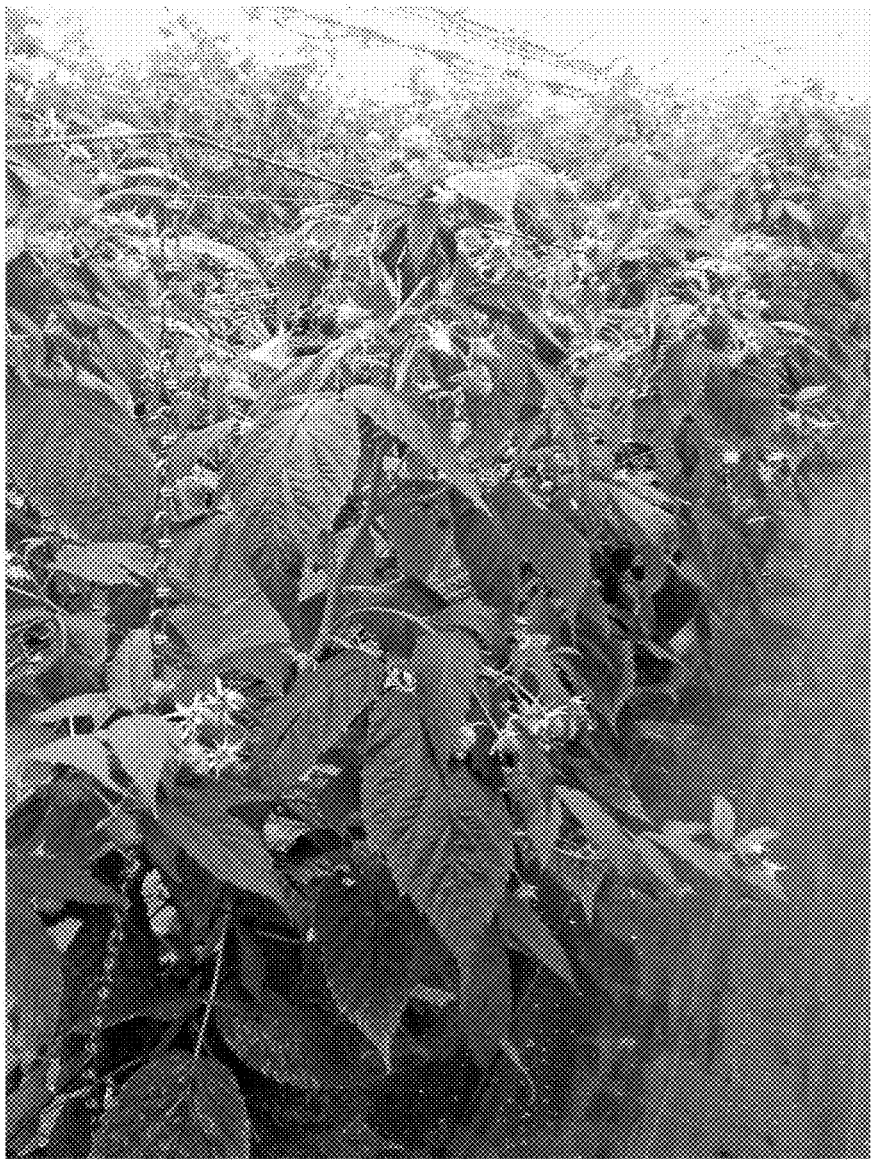

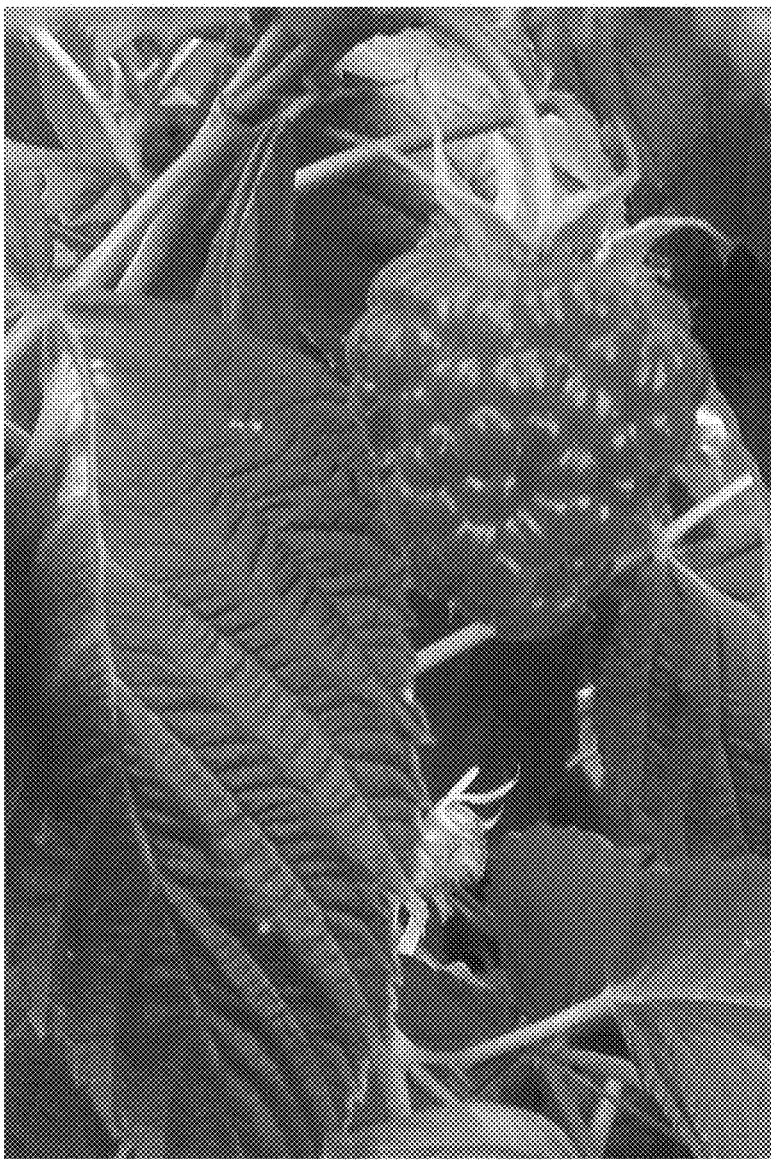

* * * * *